US 12,295,855 B2

(12) United States Patent
Taber et al.

(10) Patent No.: US 12,295,855 B2
(45) Date of Patent: May 13, 2025

(54) INTERSPINOUS IMPLANTS

(71) Applicant: Zimmer Biomet Spine, Inc., Westminster, CO (US)

(72) Inventors: Justin Taber, Lafayette, CO (US); Ryan Fredricey, Westminster, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 0 days.

(21) Appl. No.: 17/883,212

(22) Filed: Aug. 8, 2022

(65) Prior Publication Data

US 2022/0401224 A1    Dec. 22, 2022

Related U.S. Application Data

(60) Continuation of application No. 16/861,946, filed on Apr. 29, 2020, now Pat. No. 11,432,936, which is a division of application No. 15/718,298, filed on Sep. 28, 2017, now Pat. No. 10,687,954, which is a continuation of application No. 14/655,449, filed as
(Continued)

(51) Int. Cl.
*A61F 2/44* (2006.01)
*A61B 17/70* (2006.01)
*A61F 2/30* (2006.01)

(52) U.S. Cl.
CPC ........ *A61F 2/4405* (2013.01); *A61B 17/7061* (2013.01); *A61B 17/7068* (2013.01); *A61F 2/4455* (2013.01); *A61F 2002/30373* (2013.01); *A61F 2002/30405* (2013.01); *A61F 2002/30471* (2013.01); *A61F 2002/305* (2013.01); *A61F 2002/30507* (2013.01); *A61F 2002/30578* (2013.01); *A61F 2002/30777* (2013.01); *A61F 2002/30784* (2013.01); *A61F 2002/30785* (2013.01); *A61F 2002/30841* (2013.01); *A61F 2002/3093* (2013.01)

(58) Field of Classification Search
None
See application file for complete search history.

(56) References Cited

U.S. PATENT DOCUMENTS 4,041,939 A    8/1977   Hall
8,241,330 B2   8/2012   Lamborne et al.
(Continued)

FOREIGN PATENT DOCUMENTS

WO    WO 2014/106244    7/2014

OTHER PUBLICATIONS

International Search Report and Written Opinion for International (PCT) Patent Application No. PCT/US2013/078476, dated Apr. 28, 2014, 13 pages.
(Continued)

*Primary Examiner* — Tessa M Matthews
(74) *Attorney, Agent, or Firm* — Sheridan Ross P.C.

(57) ABSTRACT

The present disclosure provides a spinous process implant and associated methods. In one aspect of the disclosure, the implant includes a spacer that is connectable to two extensions. One of the two extensions is connectable to the spacer at a first end and coupled to the spacer by a rotational connection. The other of the two extensions is movably connectable to the second end of the spacer and translatable over the outer surface of the spacer from the second end.

18 Claims, 9 Drawing Sheets

Related U.S. Application Data application No. PCT/US2013/078476 on Dec. 31, 2013, now Pat. No. 9,775,718.

(60) Provisional application No. 61/747,695, filed on Dec. 31, 2012.

(56) References Cited

U.S. PATENT DOCUMENTS

| | | | |
|---|---|---|---|
| 8,382,801 B2 | 2/2013 | Lamborne et al. | |
| 8,728,123 B2* | 5/2014 | Bucci | A61B 17/7068 606/248 |
| 9,055,981 B2 | 6/2015 | Lamborne et al. | |
| 9,247,968 B2 | 2/2016 | Taber et al. | |
| 9,265,532 B2 | 2/2016 | Lamborne et al. | |
| 9,387,016 B2* | 7/2016 | Okamoto | A61B 17/7065 |
| 9,775,718 B2 | 10/2017 | Taber et al. | |
| 10,687,954 B2 | 6/2020 | Taber et al. | |
| 11,432,936 B2 | 9/2022 | Taber et al. | |
| 2003/0216736 A1* | 11/2003 | Robinson | A61B 17/7068 606/281 |
| 2006/0247640 A1* | 11/2006 | Blackwell | A61B 17/7068 606/71 |
| 2008/0045955 A1 | 2/2008 | Berrevoets et al. | |
| 2010/0241167 A1* | 9/2010 | Taber | A61B 17/7061 606/249 |
| 2011/0172711 A1* | 7/2011 | Kirschman | A61B 17/7058 606/252 |
| 2011/0224731 A1 | 9/2011 | Smisson, III et al. | |
| 2011/0264221 A1 | 10/2011 | Woodward et al. | |
| 2012/0109203 A1 | 5/2012 | Dryer et al. | |
| 2012/0136390 A1* | 5/2012 | Butler | A61B 17/7067 606/248 |
| 2012/0221050 A1 | 8/2012 | Ingalhalikar et al. | |
| 2012/0239089 A1 | 9/2012 | Druma et al. | |
| 2012/0323276 A1* | 12/2012 | Okamoto | A61B 17/7065 606/249 |
| 2013/0079880 A1 | 3/2013 | Wolters et al. | |
| 2013/0103086 A1* | 4/2013 | Marik | A61B 17/7068 606/279 |
| 2013/0158604 A1* | 6/2013 | Okamoto | A61B 17/7065 606/249 |
| 2013/0184752 A1* | 7/2013 | Binder | A61B 17/7068 606/248 |
| 2013/0184753 A1 | 7/2013 | Keiper | |
| 2013/0197581 A1* | 8/2013 | Justis | A61B 17/7068 606/279 |
| 2013/0197582 A1 | 8/2013 | Prevost et al. | |
| 2013/0304125 A1 | 11/2013 | Timm et al. | |
| 2019/0269445 A1 | 9/2019 | Singh et al. | |

OTHER PUBLICATIONS

"International Application Serial No. PCT/US2013/078476, International Preliminary Report on Patentability mailed Jul. 9, 2015", 11 pages.

Official Action for U.S. Appl. No. 14/655,449, dated Nov. 15, 2017, 18 pages.

Notice of Allowance for U.S. Appl. No. 14/655,449, dated May 31, 2017, 7 pages.

"U.S. Appl. No. 15/718,298, Preliminary Amendment filed Oct. 16, 2017", 8 pages.

Official Action for U.S. Appl. No. 15/718,298, dated Nov. 1, 2018, 7 pages, Restriction Requirement.

Official Action for U.S. Appl. No. 15/718,298, dated Apr. 12, 2019, 19 pages.

Final Action for U.S. Appl. No. 15/718,298, dated Sep. 27, 2019, 15 pages.

"U.S. Appl. No. 15/718,298, Advisory Action mailed Dec. 13, 2019", 3 pages.

Notice of Allowance for U.S. Appl. No. 15/718,298, dated Jan. 31, 2020, 6 pages.

Official Action for U.S. Appl. No. 16/861,946, dated Dec. 21, 2021, 9 pages.

Notice of Allowance for U.S. Appl. No. 16/861,946, dated Apr. 22, 2022, 7 pages.

Notice of Allowance for U.S. Appl. No. 16/861,946, dated May 13, 2022, 3 pages.

Corrected Notice of Allowance for U.S. Appl. No. 16/861,946, dated Aug. 11, 2022, 4 pages.

* cited by examiner

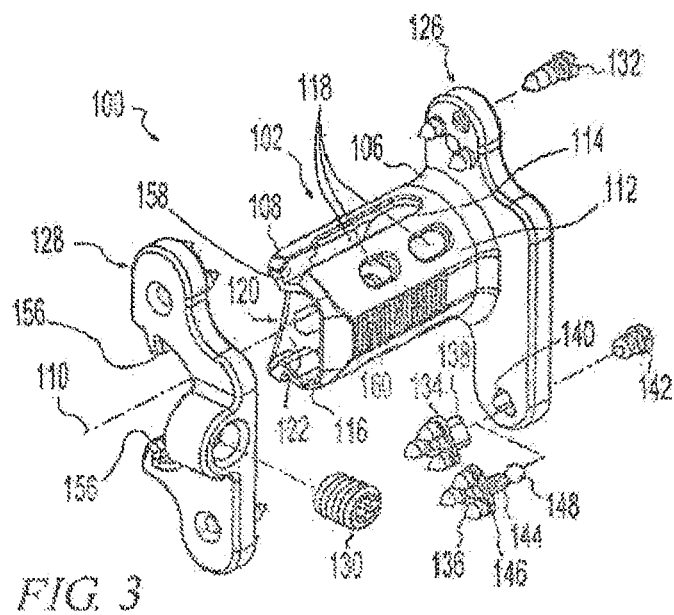

INTERSPINOUS IMPLANTS

CROSS REFERENCE TO RELATED APPLICATIONS

This application is a continuation of application Ser. No. 16/861,946, filed Apr. 29, 2020, now U.S. Pat. No. 11,432,936, which is a divisional of application Ser. No. 15/718,298, filed Sep. 28, 2017, now U.S. Pat. No. 10,687,954, which is a continuation of U.S. application Ser. No. 14/655,449, filed Jun. 25, 2015, now U.S. Pat. No. 9,775,718, which is a 371 of PCT/US2013/078476, filed Dec. 31, 2013, which claims the benefit of U.S. Provisional Application No. 61/747,695, filed Dec. 31, 2012.

This application is related to U.S. patent application Ser. No. 11/934,604, filed Nov. 2, 2007, now U.S. Pat. No. 8,241,330, titled Spinous Process Implants and Associated Methods; U.S. patent application Ser. No. 12/020,282, filed Jan. 25, 2008, titled Spinal Implants and Methods; U.S. patent application Ser. No. 12/751,856, filed Mar. 31, 2010, titled Spinous Process Implants and Associated Methods; U.S. patent application Ser. No. 12/538,710, filed Aug. 10, 2009, now U.S. Pat. No. 8,382,801, titled Spinous Process Implants, Instruments, and Methods; and U.S. patent application Ser. No. 12/854,125, filed Aug. 10, 2010, titled Interspinous Implants and Methods, all of which are incorporated herein by reference as if set out in full.

FIELD

The present disclosure relates to interspinous process implants that facilitate fusion and associated methods thereof.

BACKGROUND

The vertebrae of the human spine are arranged in a column with one vertebra on top of the next. An intervertebral disc lies between adjacent vertebrae to transmit force between the adjacent vertebrae and provide a cushion between them. The discs allow the spine to flex and twist. With age or injury, spinal discs begin to break down, or degenerate, resulting in the loss of fluid in the discs, and consequently, the discs become less flexible. Likewise, the discs become thinner allowing the vertebrae to move closer together. Degeneration also may result in tears or cracks in the outer layer, or annulus, of the disc. The disc may begin to bulge outwardly. In more severe cases, the inner material of the disc, or nucleus, may actually extrude out of the disc. In addition to degenerative changes in the disc, the spine may undergo changes due to trauma from automobile accidents, falls, heavy lifting, and other activities. Furthermore, in a process known as spinal stenosis, the spinal canal narrows due to excessive bone growth, thickening of tissue in the canal (such as ligament), or both. In all of these conditions, the spaces through which the spinal cord and the spinal nerve roots pass may become narrowed leading to pressure on the nerve tissue which can cause pain, numbness, weakness, or even paralysis in various parts of the body. Finally, the facet joints between adjacent vertebrae may degenerate and cause localized and/or radiating pain. All of the above conditions, as well as others not specifically mentioned, are collectively referred to herein as spine disease.

Conventionally, surgeons treat spine disease by attempting to restore the normal spacing between adjacent vertebrae. This may be sufficient to relieve pressure from affected nerve tissue. However, it is often necessary to surgically remove disc material, bone, or other tissues that impinge on the nerve tissue and/or to debride the facet joints. Most often, the restoration of vertebral spacing is accomplished by inserting a rigid spacer made of bone, metal, or plastic into the disc space between the adjacent vertebrae and allowing the vertebrae to grow together, or fuse, into a single piece of bone. The vertebrae are typically stabilized during this fusion process with the use of bone plates and/or pedicle screws fastened to the adjacent vertebrae.

Although techniques for placing intervertebral spacers, plates, and pedicle screw fixation systems have become less invasive in recent years, they still require the placement of hardware deep within the surgical site adjacent to the spine. Recovery from such surgery can require several days of hospitalization and long, slow rehabilitation to normal activity levels.

Rather than spinal fusion, investigators have promoted the use of motion preservation implants and techniques in which adjacent vertebrae are permitted to move relative to one another. One such implant that has met with only limited success is the artificial disc implant. These typically include either a flexible material or a two-piece articulating joint inserted in the disc space. Another such implant is the spinous process spacer which is inserted between the posteriorly extending spinous processes of adjacent vertebrae to act as an extension stop and to maintain a minimum spacing between the spinous processes when the spine is in extension. The spinous process spacer allows the adjacent spinous processes to move apart as the spine is flexed. The extension stop spacers, however, also have had limited success.

Recently, the trend has been back towards fusion devices rather than motion preservation devices. One promising recent implant is a spinous process fusion plate. Similar to the fusion implants, the spinal process fusion plate promotes fusion between adjacent vertebrae to relieve pressure on the nerve. However, unlike more conventional spinal implant systems, the spinous process fusion plate facilitates less invasive procedures than conventional spinal fusion surgery. The need still exists for improved spinous process fusion plates.

BRIEF DESCRIPTION OF THE DRAWINGS

Various examples of the technology of the present application will be discussed with reference to the appended drawings. These drawings depict only illustrative examples of the technology described more fully herein and are not to be considered limiting of its scope.

FIG. 3 is a an exploded perspective view of the implant of FIG. 1;

FIG. 4 is a posterior elevational view of similar alternatives of the implant of FIG. 1;

FIG. 5 is an anterior devotional view of the implant of FIG. 1;

DESCRIPTION OF THE ILLUSTRATIVE EXAMPLES

Figure 1:
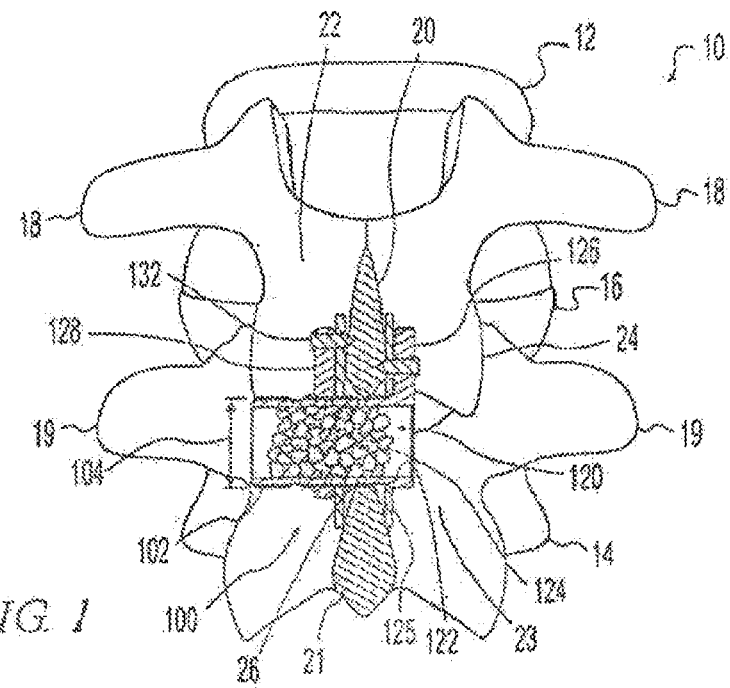
FIG. 1 is a posterior cross sectional view of an implant in situ that is consistent with the technology of the present application.

The technology of the present application will be described in the context of spinal surgery, but one of ordinary skill in the art will recognize on reading the disclosure that the technology may be applicable to other medical fields. Moreover, the technology of the present application will be described with reference to certain exemplary embodiments. The word "exemplary" is used herein to mean "serving as an example, instance, or illustration." Any embodiment described herein whether or not specifically identified as "exemplary" is not to be construed as preferred or advantageous over other embodiments. Further, the instrument(s) described in accordance with the technology of the present application facilitate surgical implantation of spinous process fusion plates. With that in mind, exemplary spinous process implants, according to the technology, may include a spacer and an extension extending outwardly from the spacer. The extension, which may be referred to as a wing, is sometimes described as being one or more lobes associated with the spacer. The extensions may include one or more openings or have a porosity that facilitates tissue in-growth to anchor the extensions to the spinous processes or other bone. The spinous process implant may be configured for insertion between adjacent spinous processes of the cervical, thoracic, and/or lumbar spine. The spacer may be provided integral with one or more of the extensions or connectable to the extensions to allow for different size spacers and extensions to be matched to accommodate patient anatomy. The spacer may be provided in a variety of sizes to accommodate anatomical variation amongst patients and varying degrees of space correction. The spacer may include openings to facilitate tissue in-growth to anchor the spacer to the vertebral bodies such as tissue in-growth from one or both of the spinous processes. The openings may be fenestrations, windows, bores, slots, or a porosity to facilitate the tissue growth. The spacer may be configured for tissue in-growth from superior and inferior spinous processes to cause fusion of the adjacent spinous processes. The openings may be relatively large and/or communicate to a hollow interior of the spacer. A hollow interior may be configured to receive bone growth promoting substances such as by packing the substances into the hollow interior. The openings may be relatively small and/or comprise pores or interconnecting pores over at least a portion of the spacer surface. The openings may be filled with bone growth promoting substances. The spacer may further include a surface that facilitates bony ongrowth or ingrowth. The surface may include, for example, a titanium plasma spray coating, surface texturing, or the like.

The extension may extend transversely from the spacer relative to a spacer longitudinal axis to maintain the spacer between adjacent spinous processes. A single extension may extend in one or more directions or multiple extensions may be provided that extend in multiple directions. One or more extensions may be adjustable longitudinally relative to one another and/or the spacer to allow the extensions to be positioned laterally relative to the spinous processes. A moveable extension may be provided that is moveable axially relative to the spacer and another extension. Alternatively, a plurality of moveable extensions may be provided. For example, the extensions may clamp against the sides of the spinous processes to immobilize the spinous processes relative to one another and promote fusion between the adjacent vertebrae. The extensions may include fasteners engageable with the spinous processes. The fasteners may include sutures, wires, pins, straps, clamps, spikes, screws, teeth, adhesives, and/or other suitable fasteners. The fasteners may be integrated into the extensions or they may be modular. Modular fasteners may be adjustable, replaceable, and/or removable to allow tailoring of the kind and quality of fixation from rigid fixation to no fixation. The spacer, extensions, and/or fasteners may advantageously be made of different materials. For example, the spacer and extensions may be made of a relatively softer material while the fasteners may be made of a relatively harder material. For example, the spacer and/or extension may be made of a polymer and/or other relatively soft material and the fastener may be made of a metal and/or other relatively hard material. In one aspect, the spacer may be made of a polyether-etherketone (PEEK) where the extensions may be made of titanium. Providing a spacer comprised of PEEK may offer benefits over other materials such as, for example, radiolucency, improved stress shielding, and the like. Providing extensions comprised of titanium may maintain the regulatory strength requirements.

Insertion of spinous process implants may be facilitated by a set of instruments alternately engageable with one another to increase the interspinous space and engageable with a spinous process implant as described in the related applications incorporated by reference. Some instrument sets may include different instrumentation for (1) placing or inserting the spinous process implant into the appropriate position and (2) compressing or translating one or both of the plates of the spinous process implant so they engage the adjacent spinous processes. Switching between instruments can either add time to the surgical procedure or require the hands of a second surgeon or assistant. Alternatively, a single insertion and compression instrument may be provided. The single insertion and compression instrument moreover is hinged or articulated to allow for one or both extensions and/or the fasteners on the extensions (as explained further below) to angle in the coronal plane as needed. The single instrument to insert and compress the implant is configured to hold the implant assembled. The supraspinous ligament generally must be sacrificed to allow the insertion of the assembled implant to the interspinous space. The implant must provide sufficient clearance so that the fasteners on the plates clear the spinous processes as the implant is inserted into the interspinous space from a generally posterior to anterior direction. Sufficient clearance is provided, for example, when the fastener(s) can be placed on opposite sides of a spinous process without cutting into or engaging the spinous process during the implant insertion. Once the implant is positioned, the compression of the handle causes the fasteners on the plate to bite into the spinous processes. The compressor may be hinged to allow for polyaxial orientation of the extension(s) or fasteners with respect to the spinous processes to facilitate differing sizes and thicknesses of the spinous processes. Additionally, in certain aspect of the invention, the implant may be inserted through a lateral or paramedian surgical access.

Reference will now be made to FIGS. 1-9 describing an exemplary embodiment of a spinous process implant for which the instruments of the present application may be used. While a specific exemplary embodiment is provided herein, implants associated with any of the incorporated applications or similar spinous process fusion plates may benefit from the technology of the present application.

Figure 2:
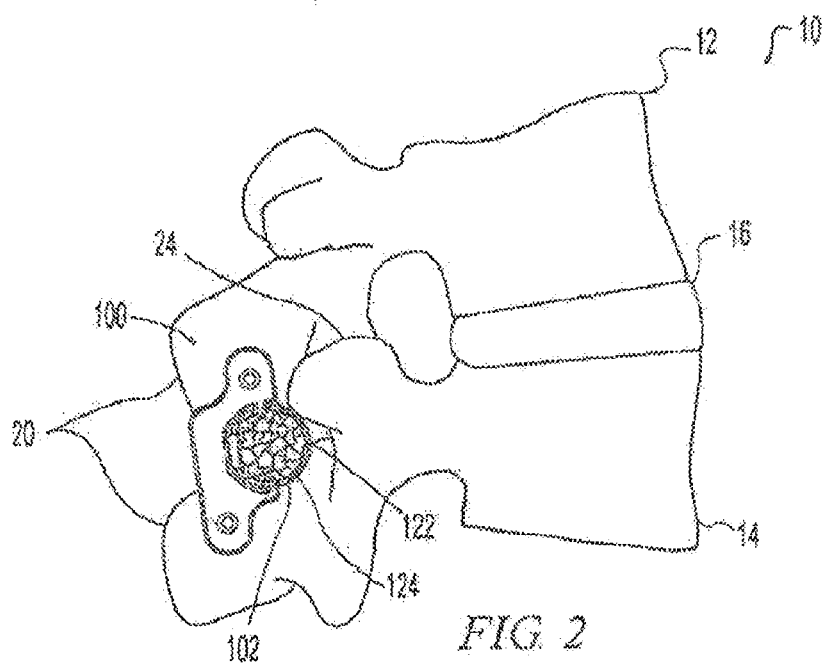
FIG. 2 is a side elevational view of the implant of FIG. 1 in situ.

FIGS. 1 and 2 depict posterior and lateral views of a pair of adjacent vertebrae of the lumbar spine 10. A superior vertebra 12 is separated from an inferior vertebra 14 by a disc 16. Each vertebra includes a pair of transverse processes 18, 19, a posteriorly projecting spinous process 20, 21, and a pair of lamina 22, 23 connecting the transverse processes 18, 19 to the spinous process 20, 21, In addition to the connection through the disc 16, the vertebrae 12, 14 articulate at a pair of facet joints 24.

FIGS. 1-9 illustrate an exemplary spinous process implant 100. The implant 100 includes a spacer 102 positioned between the spinous processes 20, 21. As mentioned above, the spacer 102 may be formed from PEEK or other biocompatible ceramic or synthetic material. The geometry of the implant 100 is illustrated with the use of axes that define length (l), height (h), and width (w) directions for the spacer. When implant 100 is implanted in a patient, the height direction of the spacer 102 is generally oriented along the superior/inferior direction of the patient's anatomy, the width direction of the spacer 102 is generally oriented along the anterior/posterior direction of the patient's anatomy, and the length direction of the spacer 102 is generally oriented along the lateral/medial direction of the patient's anatomy.

The height 104 (FIG. 1) of spacer 102 limits how closely the spinous processes 20, 21 can move together. As the implant in this example includes one or more fusion plates directly coupled to the spinous processes and the spacer, the height also limits how distantly the spinous processes 20, 21 can move apart. Thus, the spacer 102 maintains a minimum and maximum distance between the spinous processes 20, 21. In the case of spine disease involving posterior subsidence of the adjacent vertebra, insertion of the spacer 102 between the spinous processes 20, 21 will move the vertebrae apart and relieve pressure on nerve tissue and the facet joints 24.

Figure 14:
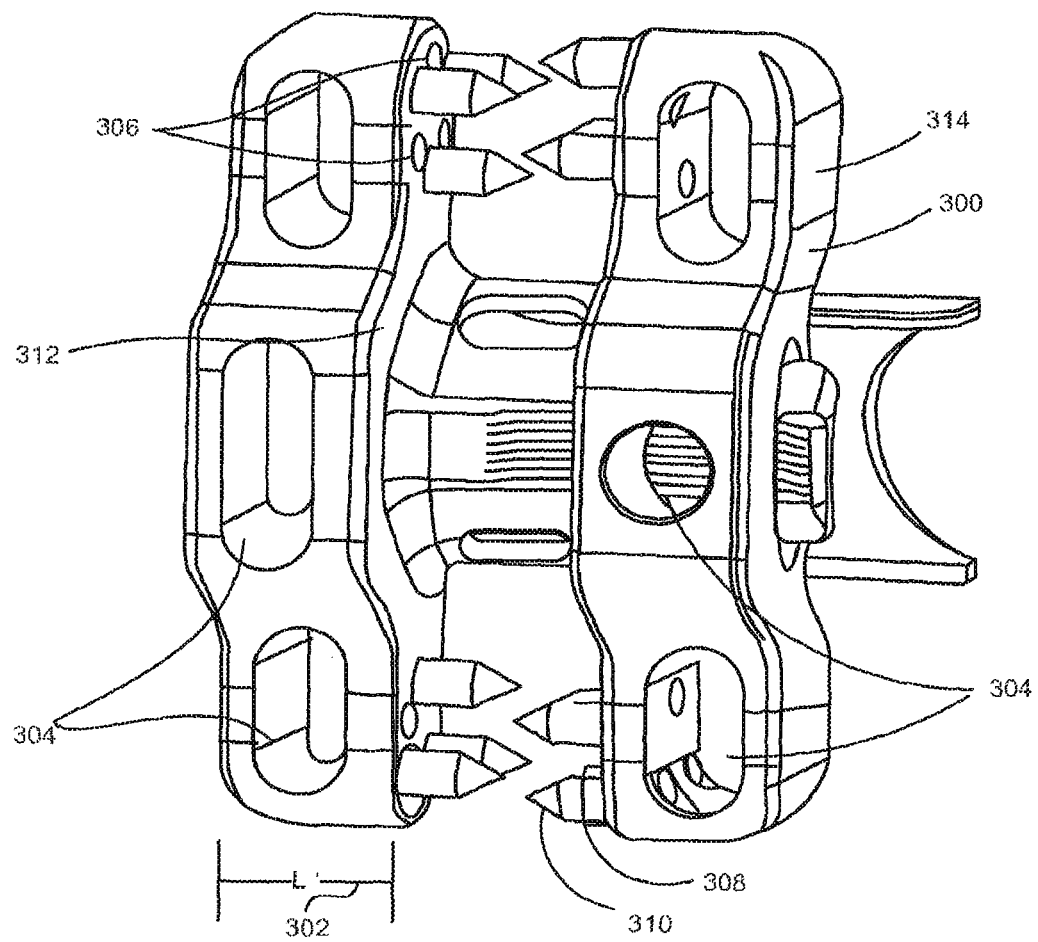
FIG. 14 is a perspective view of an implant consistent with the technology of the present application.

As shown in FIG. 3, the spacer 102 includes a first end 106, a second end 108, and a longitudinal axis 110 extending from the first end to the second end. The spacer 102 has a sidewall 112, generally parallel to the longitudinal axis 110, including superior and inferior outer surfaces 114, 116. Transverse openings 118 (see also FIG. 6) communicate from the superior and inferior outer surfaces 114, 116 inwardly to facilitate tissue in-growth. As shown in FIG. 14), extensions 300 may include fenestrations 304 similar to transverse openings 118 to allow tissue in-growth to facilitate connectivity between the extensions and the spinous processes. The exemplary spacer 102 includes a hollow interior 120 bounded by an inner surface 122 such that the openings 118 communicate from the outer surfaces 114, 116 to the hollow interior 120. Bone growth promoting substances 124 are shown packed into the hollow interior 120 in FIGS. 1 and 2 to promote fusion of the vertebrae 12, 14 by bone growth between the spinous processes 20, 21.

The spinous process implant 100 further includes a first extension 126 projecting outwardly from the spacer 102 along the spacer height direction h and transversely to the longitudinal axis 110 to lie generally alongside the superior and inferior spinous processes 20, 21. Abutment of the first extension 126 with the spinous processes 20, 21 helps prevent lateral movement of spacer 102, thereby maintaining spacer 102 between the spinous processes 20, 21. In the exemplary spinous process implant 100, the first extension 126 is fixed relative to the spacer 102 and the implant includes a second extension 128 mountable to the spacer for axial movement relative to the first extension 126. The second extension 128 may be moved toward the first extension 126 to approximate the width of the spinous processes 20, 21 and better stabilize the implant 100. It is fixed in place by tightening a set screw 130 (FIG. 3) against the spacer 102. The extensions 126, 128 include fasteners 132, 134, 136 projecting from the extensions 126, 128 to engage the spinous processes 20, 21 to fix the spacer 102 to the spinous processes 20, 21. FIG. 1 depicts an additional bone growth promoting substance in the form of strips of bone 125 sandwiched between the extensions 126, 128 along the sides of the spinous processes 20, 21 to promote bone growth along the sides of the spinous processes to further enhance fusion of the vertebrae 12, 14. The extensions 126, 128 preferably extend inferiorly as well as superiorly from spacer 102 to optionally attach to the inferior spinous processes to immobilize the spinous processes 20, 21 relative to one another while fusion takes place.

Fasteners 132, 134, and 136 may take any suitable form. The fasteners, similar to the spacer and extensions may include openings, channels or a porosity to facilitate tissue in-growth. They may be made integral with the extensions 126, 128 such as by machining or casting them with the extensions or they may be formed separately and permanently attached to the extensions 126, 128. Fastener 132 is a sharpened spike that threadably engages the extension 126. The threaded engagement allows the fastener 132 to be replaced with a different fastener 132. For example, the fastener 132 may be replaced by one that has a different shape, a different size, a different material, or a different surface coating. The threaded engagement also allows the fastener 132 to be adjusted to extend by varying amounts from the extension 126 to vary how it engages the bone. Thus, the fastener 132 can be adjusted to fit differently shaped bones or to penetrate into a bone by varying amounts. For example, multiple threaded fasteners 132 can be adjusted to extend by different amounts to conform to curved or angled bone. Finally, the threaded engagement allows the user to remove the fastener 132 when fixation is not desired such as when it is desired to use implant 100 in a non-fusion procedure as an extension stop without limiting flexion.

As best seen in FIG. 3, fasteners 134 and 136 are provided as multi-spike pods allowing a plurality of spikes to be quickly adjusted, changed, or omitted. Fastener 134 includes a non-circular tab 138 engageable with a non-circular opening 140 in the extension 126. The non-circular engagement prevents the fastener 134 from rotating. The tab 138 may form a press-fit, snap-fit, or other suitable engagement with the opening 140. The tab 138 may be further secured by a supplemental screw 142. Fastener 136 includes a threaded shaft 144 threadably engaged with a base member 146 to allow the length of the fastener 136 to be adjusted. The shaft 144 engages the extension 126 in a rotating and pivoting manner such that the fastener 136 can be adjusted rotationally and angularly to engage the bone surface. In the illustrative embodiment, the shaft 144 terminates in a spherical ball 148 that engages the opening 140 in a ball-and-socket arrangement for three degrees of freedom. However, any mechanism that allows any number of degrees of freedom may be used. The fastener 136 may be allowed to move in use so that as the extension 126 is pressed toward a bone, the fastener 136 adjusts to the angle of the bone surface. The fastener 136 also may be secured such as by screw 142 to adjust the tension in the joint and/or to lock the fastener 136 in a predetermined orientation.

FIG. 4 illustrates the axial relationship of fasteners on the opposing extensions 126, 128. In the illustrative implant 100, the fasteners 132 at the top of the implant 100 are shown aligned along a common axis 150 that is substantially perpendicular to extensions 126 and 128. The fasteners 134 at the bottom of the implant 100 are shown offset so that they can interleave, if necessary, as they are pressed into a bone. Any combination of fastener type, number, and alignment may be provided on the implant 100.

Figure 6:
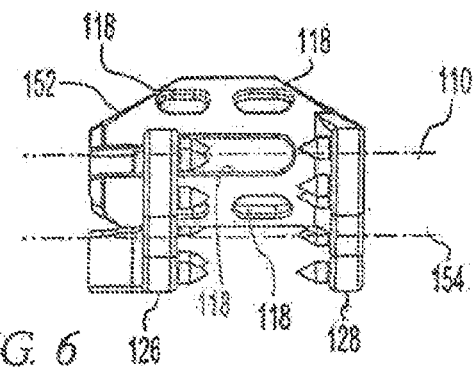
FIG. 6 is a top plan view of the implant of FIG. 1.

As seen in FIGS. 5 and 6, the ends 106, 108 of the spacer 102 include anterior chamfers 152. These chamfers 152 allow the ends 106, 108 to clear posteriorly facing structures of the vertebrae 12, 14 such as the facet joints 24. Also, as seen in FIGS. 5 and 6, the spacer 102 is offset anteriorly (in the spacer width direction w) relative to the extensions 126, 128 such that the longitudinal axis 110 of the spacer 102 is anterior of a midline plane 154 (FIGS. 6, 8) of the extensions 126, 128. The anterior offset of the spacer 102 allows it to fit deeply between the spinous processes 20, 21 while the extensions 126, 128 fit alongside the spinous processes 20, 21.

Figure 7:
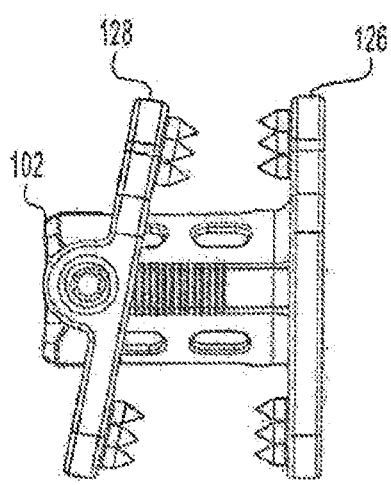
FIG. 7 is a posterior elevational view of the implant of FIG. showing the assembly in an alternate position.
Figure 8:
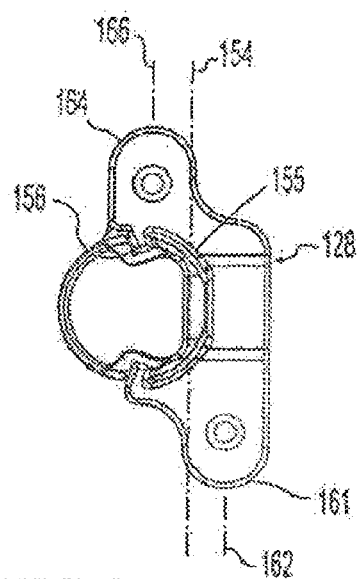
FIG. 8 is a side elevational view of the implant of FIG. 1.

As best seen in FIGS. 3 and 8, the second extension 128 defines an aperture 155 conforming generally to the cross-sectional shape of the spacer 102. In the illustrative embodiment of FIGS. 1-9, the aperture 155 opens anteriorly to form a "C"-shape. Tabs 156 extend inwardly from the superior and inferior portions of the aperture to slidingly engage elongated slots 158 in the superior and inferior surfaces of the spacer 102. The second extension 128 can be translated longitudinally along the spacer length 1 toward and away from the first extension 126. Tightening the set screw 130 against the posterior side 160 of the spacer 102 forces the tabs 156 posteriorly against the sides of the slots 158 and locks the second extension 128 in place longitudinally. The posterior side 160 of the spacer 102 may be roughened as shown to better grip the set screw 130. The set screw 130 may also dig into the surface of the spacer 102 upon tightening to positively grip the spacer 102. The aperture 155 (FIGS. 3, 8) may conform closely to the spacer 102 to constrain the second extension 128 to generally parallel motion relative to the first extension 126. Alternatively, the aperture 155 may be larger than the spacer 102 by a predetermined amount to permit a predetermined amount of angular adjustment of the second extension 128 relative to the first extension 126 as shown in FIG. 7 to allow the extension 128 to adjust to the underlying bone surface. In alternative embodiments, second extension 128 is generally "O" shaped instead of "C" shaped such that the aperture surrounds the spacer. In this manner, spacer 102 slides completely within aperture 155. In these embodiments, second extension 128 may include a single tab 156 which engages a single slot 158 within spacer 102. Alternatively, two or more tabs 156 may be used, extending inwardly into aperture 155 at desired locations to engage corresponding slots 158. It will be appreciated that generally "O" shaped apertures include any shape of aperture into which spacer 102 is received whereby the structure of second extension 128 surrounds spacer 102 and permits translation of second extension 128 along spacer 102.

Figure 9:
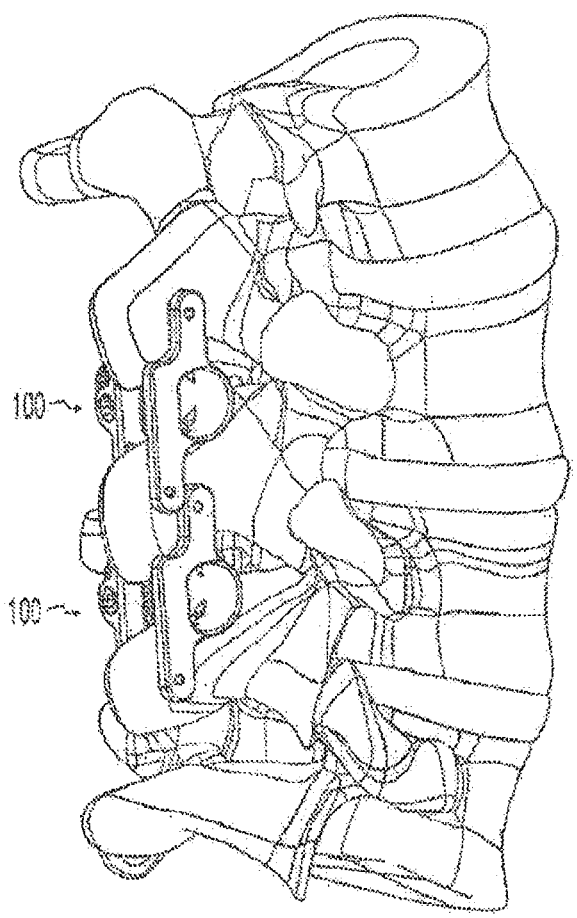
FIG. 9 is a perspective view of a pair of implants like that of FIG. 1 in situ.

As best seen in FIG. 8, the second extension 128 includes a first inferior lobe 161 having a first lobe centerline 162 and a second superior lobe 164 having a second lobe centerline 166. In the illustrative embodiment, the first lobe centerline 162 and the second lobe centerline 166 are parallel and spaced apart so that the second extension 128 has a generally "Z"-shaped plan form. This shape allows the extension of one implant 100 to interleave, if necessary, with another implant 100 in a multilevel surgery (as shown in FIG. 9) to permit close spacing of the implants, and/or longer extension lobes for more extensive bone engagement. In addition, first inferior lobe 161 has a semi-circular convex shape that is generally complementary to a semi-circular superior concave surface 165 formed adjacent second superior lobe 164. Similarly, second superior lobe 164 has a semi-circular convex shape that is generally complementary in shape to a semi-circular inferior concave surface 163 formed adjacent first inferior lobe 161. As indicated in FIG. 8, first inferior lobe 161 is adjacent to inferior concave surface 163, and extension midline plane 154 is located between first inferior lobe 161 and inferior concave surface 163. Second superior lobe 164 is adjacent superior concave surface 165, and extension midline plane 154 is located between second superior lobe 164 and superior concave surface 165. Moreover, first inferior lobe radius $r_1$ is substantially equal to superior concave surface radius $r_4$, while second superior lobe radius $r_3$ is substantially equal to inferior concave surface radius $r_2$. As a result, when two implants are placed on adjacent spinal levels, the first inferior lobe 161 of the upper implant may be (but need not be, depending on what is medically indicated) interfitted into the superior concave surface 165 of the inferior implant. In addition the second superior lobe 164 of the inferior implant may be interfitted into the inferior concave surface 163 of the superior implant. In the illustrative example of FIGS. 1-9, first inferior lobe 161 and second superior lobe 164 form a unitary second extension 128. Although not separately depicted, first extension 126 also has complementary lobes that are similarly configured and oriented relative to one another.

As shown in FIG. 9, multiple spinous process implants 100 may be placed on adjacent levels of the spine. As illustrated in the figure, a first superior implant 100 is positioned with its spacer 102 between a first superior spinous process and a second intermediate spinous process, while a second inferior implant 100 is positioned with its spacer 102 between the second intermediate spinous process and a third inferior spinous process. The first extensions 126 of the superior and inferior implants are located on a first side of the patient's sagittal plane, while the second extensions 128 of the superior and inferior implants are located on a second side of the patient's sagittal plane.

In the illustrative embodiment of FIGS. 1-9, the extension lobe centerlines 162, 166 are offset equidistantly from the midline plane 154 of the second extension 128. Although not separately shown, the first extension 126 is configured similarly. The centerlines 162, 166 may vary from parallel and they may be offset asymmetrically to form different shapes to accommodate different vertebral anatomy. For example, the shape may be tailored for different portions of the spine 10. In the illustrative embodiment of FIGS. 1-9, the first extension 126 has the same shape as the second extension 128. However, the shape may be varied between the first and second extensions 126, 128.

As shown in for example, FIGS. 2, 3, 8, and 9, the first extension 126 and second extension 128 may have tool connection points 168 and 170. The tool connection points 168 and 170 are shown as dimples or bores in the exemplary embodiment and are cooperatively shaped to engage an associated prong, tab or protrusion on the insertion/compression instrument as will be explained further below.

Figure 10:
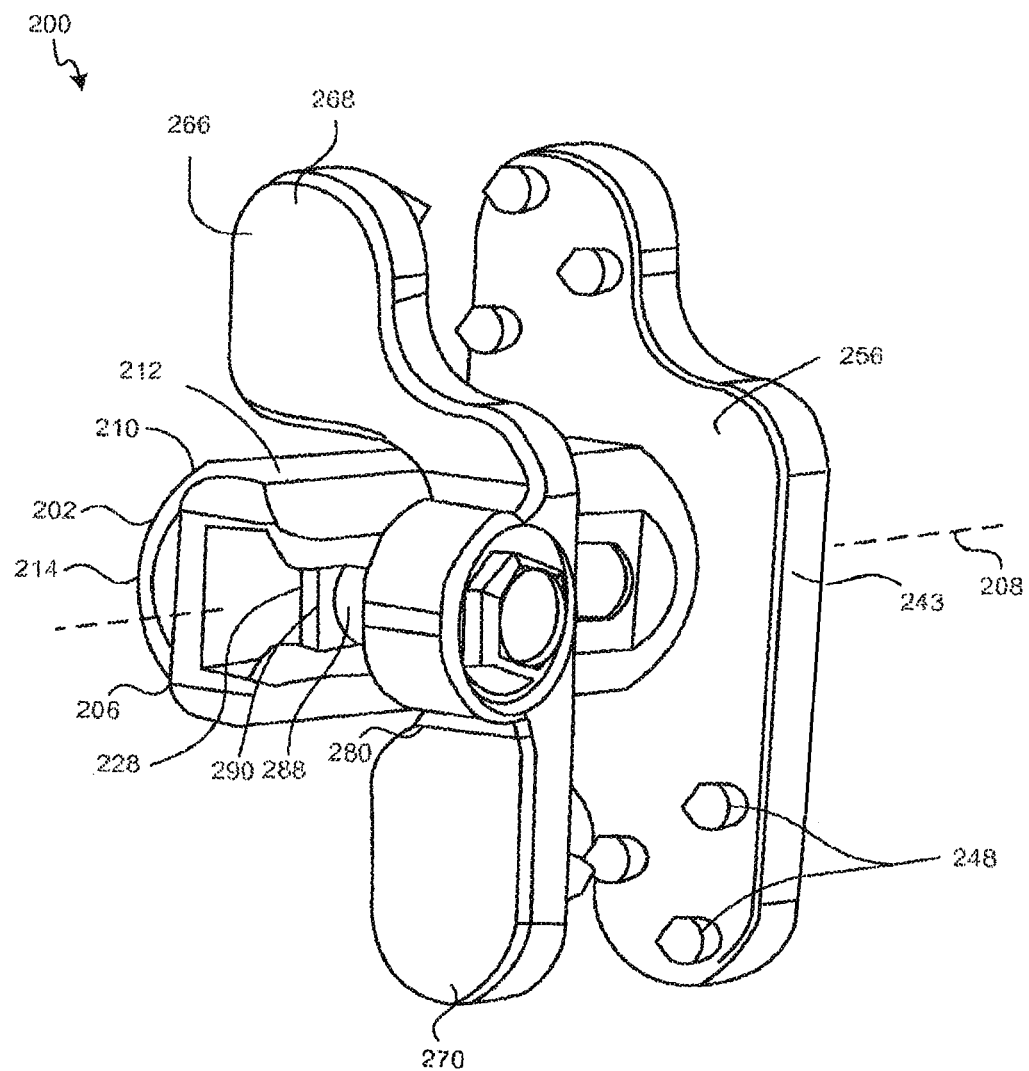
FIG. 10 is a perspective view of an implant that is consistent with the technology of the present application.
Figure 11:
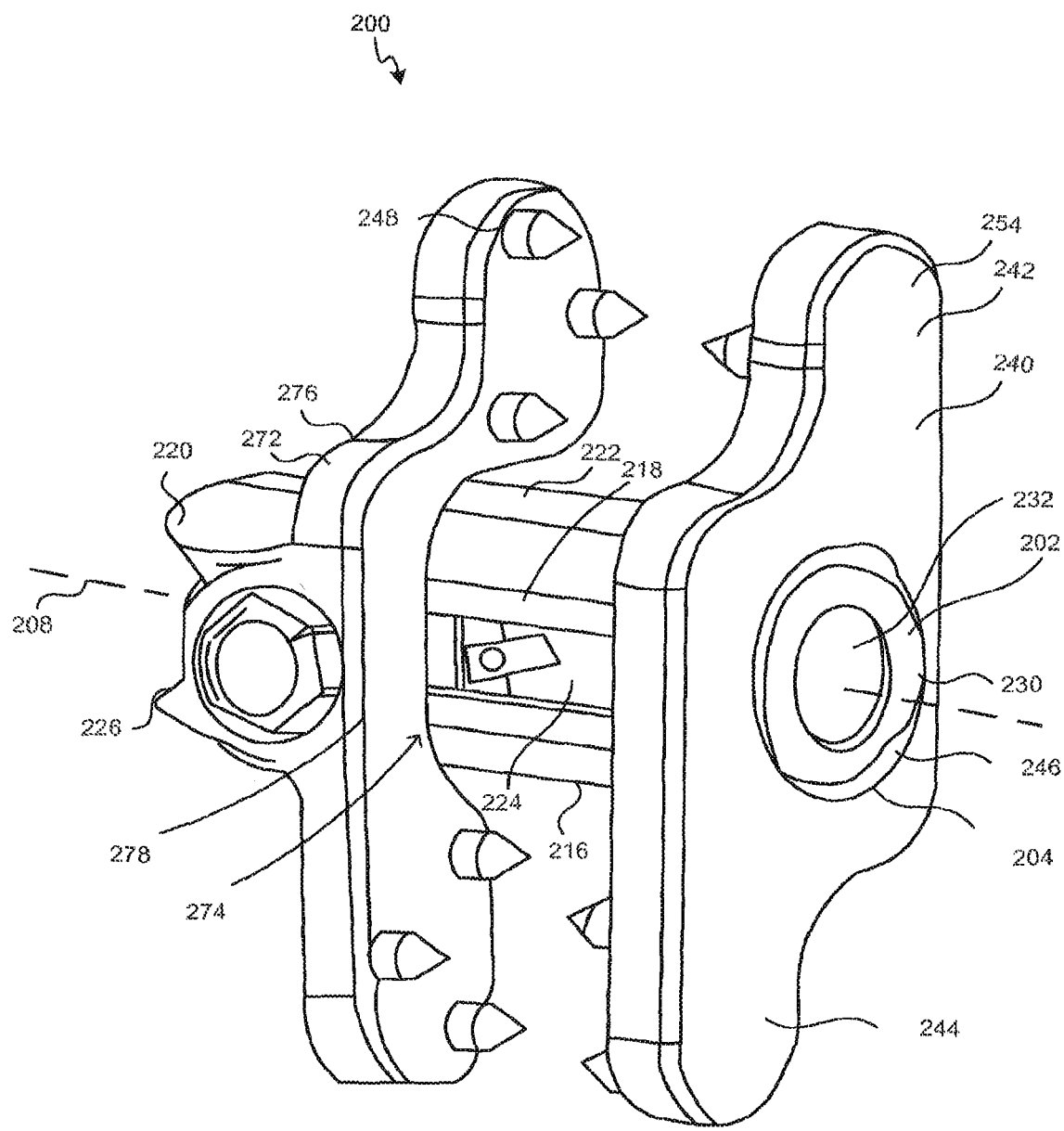
FIG. 11 is a perspective view of the implant of FIG. 10.

FIGS. 10 and 11 depict left and right perspective posterior views of another exemplary spinous process implant 200.

The implant 200 includes a spacer 202 that is adapted to be positioned between spinous processes, such as spinous processes 20, 21 above. The spacer 202 may be formed of a synthetic, ceramic, or composite material such as, for example, PEEK or other similar plastics. In other aspects, the spacer 202 may be formed from bone, such as an allograph, or other biocompatible materials.

The spacer 202 includes a first end 204 and a second end 206 opposite the first end 204. The second end 206 is a length L (FIG. 12) along a longitudinal axis 208 from the first end 204. The length L is such that the first end 204 of the spacer 202 is adapted to be positioned on a first side of the interspinous space and the second end 206 of the spacer 202 is adapted to be positioned on a second side of the interspinous space. The spacer 202 has at least one sidewall 210. The sidewall forms a generally cylindrical shape in this exemplary embodiment. The sidewall 210 may form a superior surface 212, an anterior surface 214, an inferior surface 216, and a posterior surface 218. The surfaces may be generally curved as shown or generally flat with chamfered edges 220 to reduce tissue trauma. The superior, anterior, inferior, and posterior surface 212, 214, 216, and 218 may form a continuous curve or have multiple radii. The sidewall 210 forms a hollow chamber 211.

The sidewall 210 forms a hollow chamber 211. Each of the surfaces 212, 214, 216, and 218 may incorporate one or more openings 222 in communication with the hollow chamber 211 to facilitate tissue in-growth. The tissue in-growth facilitates fusion between the spinous processes. In the exemplary embodiment shown, each of the openings 222 are shown as a single elongated slot. The openings 222 may be a single elongated slot, multiple elongated slots, bores, perforations, pores, micro-pores, or the like. In this exemplary embodiment, the posterior surface 218 also includes an elongated slot 224 that extends from the first end 204 to the second end terminal edge 226 located at the distal most portion of the second end 206. The elongated slot 224 extending to the terminal edge 226 facilitates implantation of implant 200 as will be explained further below. Generally, other slots would not extend to the terminal edge 226 for strength considerations. In certain aspects, the elongated slot 222 on another surface may extend to the terminal edge 226 instead of the elongated slot 224 on posterior surface 218.

The second end terminal edge 226 forms an opening 228 to allow lateral access to hollow chamber 211 from the second end 206. The first end 204 includes a first end terminal edge 230. The first end terminal edge 230 forms an opening 232 to allow lateral access to hollow chamber 211 from the first end 204. The openings 228, 232 may be considered to define a plane perpendicular to the longitudinal axis 208. The sidewall 210 of the spacer 202 extends from the openings 228, 232 parallel to the longitudinal axis 208.

Figure 12:
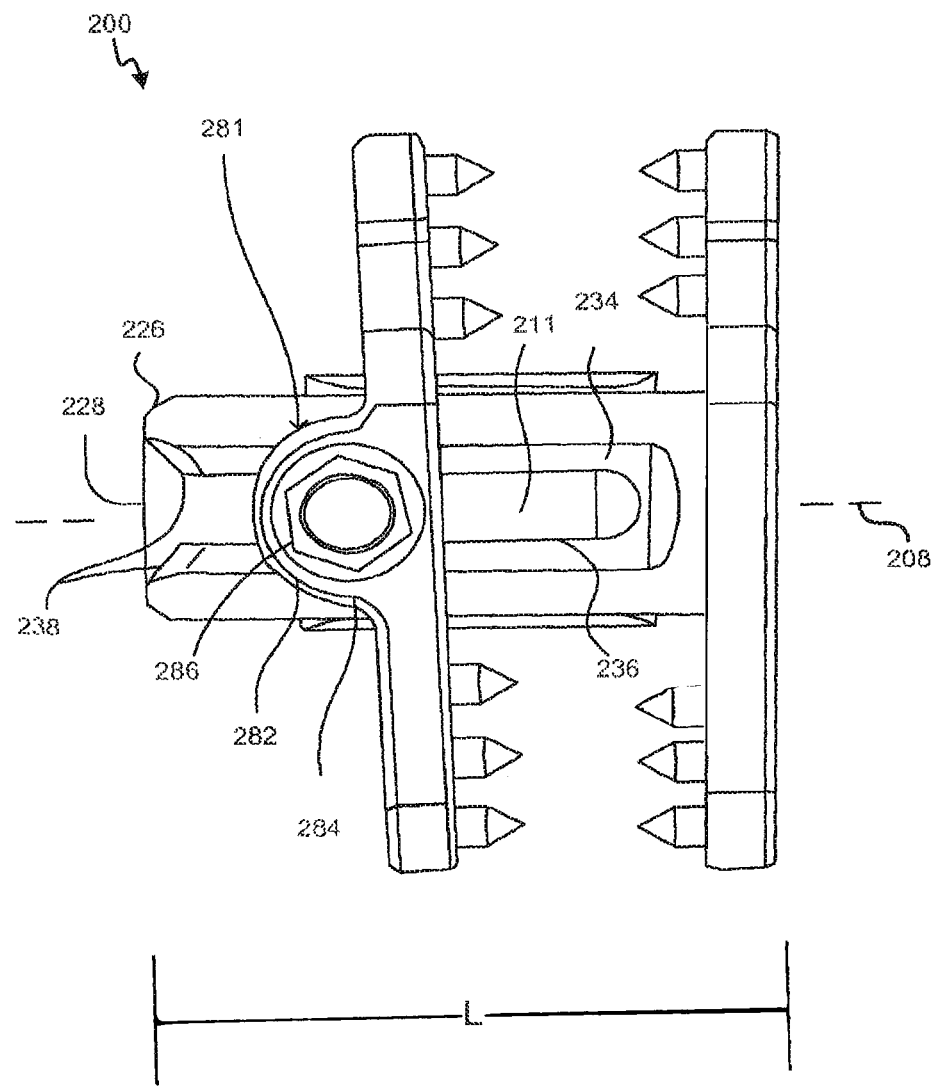
FIG. 12 is a posterior view of the implant of FIG. 10.

As can be best seen in FIG. 12, which provides a posterior view of implant 200, the elongated slot 224 on the posterior surface 218 is generally defined by a superior edge 234 and an inferior edge 236 that extends substantially in parallel from the first end 204 to the second end 206. In this exemplary embodiment, as the superior and inferior edges 234, 236 approach the terminal edge 226, the superior and inferior edges 234, 236 diverge to form a "V" shaped taper 238, which may act as a guide as will be explained further below.

The implant 200 further comprises a first extension 240 projecting outwardly from the spacer 202. In some embodiments, first extension 240 comprises a material different than that of spacer 202. In a particular embodiment, first extension comprises titanium, stainless steel, or other biocompatible metals. The first extension 240, which may sometimes be referred to as a wing, includes a superior lobe 242 and an inferior lobe 244 extending from a rectangular or square main body 243. The main body 243 may be other shapes including elliptical, trapezoidal, or the like. Moreover, the edges of any polygonal shape are generally beveled or rounded to reduce tissue trauma. The superior lobe 242 is offset from the inferior lobe 244 in the anterior-posterior direction to allow interleaving of multiple implants 200. In this case, the superior lobe 242 is anterior of the inferior lobe 244 although the inferior lobe 244 may be anterior to the superior lobe 242 in certain aspects. The main body 243 of the first extension 240 includes an aperture 246, which is shown as a bore that completely surrounds the spacer 202. The aperture 246 may be open in one or more directions, however. The aperture 246 may be, for example, "C" shaped, "O" shaped, "U" shaped, "D" shaped, or the like. The spacer 202 is slidingly received and mechanically locked to the first extension 240 as will be explained further below. Because the first extension 240 is mechanically locked to the spacer, the first extension 240 is sometimes referred to as the post plate. The first extension 240 also comprises one or more fasteners 248. The fasteners 248 may be similar to the fasteners 132, 134, and 136 explained above.

Figure 13:
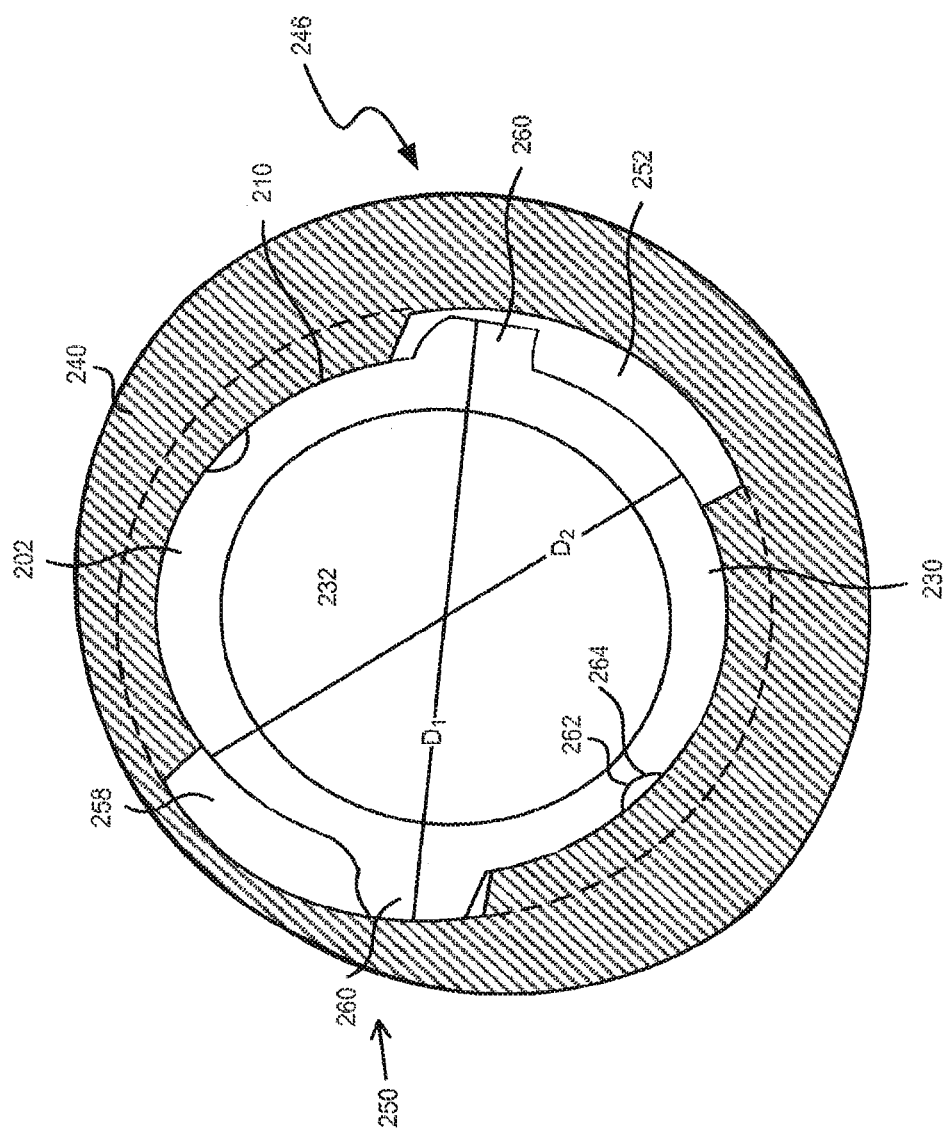
FIG. 13 is detail of a portion of the implant of FIG. 10 showing a connection between an extension and a spacer consistent with the technology of the present application.

As mentioned above, implant 200 may have a mechanical lock between spacer 202 and first extension 240. With reference to FIG. 13, an exemplary mechanical lock 250 between the spacer 202 and the first extension 240 is provided. FIG. 13 provides only a partial cut-away of the first extension 240 about the aperture 246. As shown, the aperture 246 is shaped to rotationally receive the spacer 202. A lock groove 252, of which only a portion is visible and of which a portion is shown in phantom, extends about the periphery of the aperture 246. The lock groove 252 extends between a lateral side 254 and a medial side 256 of the first extension 240. The lock groove 252 is visible at cut-Amway portions 258 on the lateral side 254 of the first extension. The spacer 202 has one or more protrusions 260 extending from the outer surface of sidewall 210. The protrusions 260 fit into cut-away portions 258 and may be rotated into lock groove 252. The protrusions 260 and lock groove 252 may be correspondingly tapered to form a taper lock or Morris lock on rotation of the spacer 202 in the aperture 246. In other embodiments, a lock washer may be used in the lock groove 252 to provide the friction fitting on rotation such that the spacer 202 and the first extension 240 form a rigid unit on rotation of the spacer 202. Alternatively, the aperture may have dimples 262, sometimes referred to as tabs, that engage with a detent 264, which may be referred to as a fenestration, in the outer surface of sidewall 210 to form a snap lock between the spacer 202 and the first extension 240 on rotation.

In this exemplary embodiment, the protrusions 260 provide a first diameter $D_1$. The first diameter is generally greater than the diameter of the aperture 246, but fits within the diameter of the lock groove 252. The sidewall 210, in this exemplary embodiment, provides a second diameter 132 that is less than the first diameter $D_1$ that is approximately equal to the diameter of the aperture. The protrusions 260 thus fit through the cut-away portions 258 and engage the medial side of the lock groove 252 to prevent the spacer 202 from being inserted through the aperture 246. Alternatively, the aperture 246 could be a countersunk bore with a shoulder and the first end terminal edge 230 may have a flanged surface or a lip to engage the countersunk bore to inhibit the spacer 202 from being inserted through the aperture 246.

The implant 200 also comprises a second extension 266. In some embodiments, second extension 266 comprises a same material as first extension 240, while in alternative embodiments the second extension comprises a different material. As shown, the second extension 266 is somewhat a mirror image of first extension 240 in that the second extension 266 has a superior lobe 268 and an inferior lobe 270 that are mirror images of the superior and inferior lobes 242, 244 of the first extension. While shown as mirror images, asymmetrical designs are possible as well, Connecting the superior lobe 268 and the inferior lobe 270 is a span 272 extending between the superior and the inferior lobes 268, 270. The span 272 is formed to provide a space 274 to cooperatively fit the spacer 202. As shown, the span 272 has a superior portion 276 generally adjacent the superior surface 212, a posterior portion 278 generally adjacent the posterior surface 218, and an inferior portion 280 generally adjacent the inferior surface 216. A second span or a continuation of the span 272 may be generally adjacent the anterior surface 214 to fully encompass the spacer 202 instead of providing a space 274 as shown. The second extension 266 also may have one or more fasteners 248 similar to the first extension 240.

The second extension 266 has a mechanical lock 281 to the spacer 202. The mechanical lock 281 in one aspect comprises a lock bore 282 on the second extension 266 that is adapted to receive a lock bolt 284. The lock bolt 284 comprises a head 286 and a shaft 288. The head 286 is rotationally retained in lock bore 282. The shaft 288 extends through the lock bore 282 into the space 274. A nut 290 is attached to the end of shaft 288. The nut 290 has a surface area with a height (superior/inferior direction in this exemplary embodiment) that extends beyond the height of a gap G formed by the elongated slot 224. The lock bore 282 and lock bolt 284 may be cooperatively threaded as well. The second extension 266 is guided onto the spacer 202 by fitting the spacer 202 into the space 274 and by moving the shaft 288 between the nut 290 and the head 286 into the V shaped taper 238. The shaft 288 is directed to the elongated slot 224 by the V shaped taper 238 and the second extension 266 is moved to the appropriate position by a surgeon. Once positioned and clamped such that the fasteners 248 bite into the spinous/processes, such as spinous processes 20, 21, the surgeon rotates the head 286 which causes the nut 290 to clamp the sidewall 210 between the nut and the anterior portion of the span 272 locking the second extension 266 in place. Because the second extension 266 is locked in position, the second extension 266 is sometimes referred to as a lock plate.

Generally, the above described implants 100, 200 relate to fusion devices where it is desirous to promote fusion by bone or tissue in-growth from the superior spinous process to the inferior spinous process by providing channels, pores, or openings to promote the fusion process. Referring now to FIG. 14, exemplary extensions 300 are provided. The extensions 300 may be modified or designed to be used with any of the first, second, or other extensions associated with this or the related application all of which are incorporated herein by reference as if set out in full. For reference, the extensions have a medial surface 312 and a lateral surface 314.

The extension 300 has a length 302 in the medial/lateral direction of L'. The length 302 is sufficient for the material of extension 300 to support fenestrations 304, which are in the form of orifices. The fenestrations 304 are shown as through holes in the anterior/posterior direction of the extension 300, but could be hollow cavities with access ports rather than through holes. The fenestrations 304 allow for packing of bone growth material, such as bone-chips, or the like as explained throughout the application and facilitate tissue growth from at least the lateral faces of the spinous processes and possibly other aspects of the vertebral body as well including, for example, the lamina. To further facilitate tissue in-growth, the extension 300 comprises bores 306, which may be a through hole or perforation as shown or a material having porosity. The surface may include, for example, a titanium plasma spray coating, a hydroxyapatite coating, surface texturing (micro or macro), other bone growth promoting coatings, a combination thereof, or the like. To further promote tissue growth, a washer 308 or washers 308 formed from a tissue growth promoting substance may be provided. The washer 308 is shown on a shaft portion of a fastener 310. Instead of the washer(s) 308, a bone plate or the like could be placed between the extensions 300 and the spinous process.

As shown in FIG. 14, the extensions 300 have a medial surface 312 and a lateral surface 314. The medial and lateral surface 312, 314 are generally planar surfaces, although in certain aspects, the medial and lateral surfaces 312, 314 may form multiple planar surfaces. To further facilitate bone growth between the spinous processes and the medial surfaces 312, the medial surfaces may have one or more portions that are concave or form a recess in the medial surface(s) 312. The recesses or concavities may receive bone ingrowth and the like.

Implants and instruments of the present disclosure may be used alone, or in conjunction with other implants and instruments. In one embodiment, an interbody device is implanted in a patient during a lateral procedure. In this procedure, the patient is placed on their side for a lateral approach to the spine to deliver the interbody between two adjacent vertebrae. Once the interbody is placed, supplemental fixation devices may be applied to the patient to further stabilize the spinal segment to be fused. In a particular embodiment, the patient remains on their side and an implant is inserted using an instrument. In this manner, a single instrument may be used to both insert and compress the implant across adjacent spinous processes to provide supplemental fixation at the treated spinal segment. The use of a single tool allows the surgeon to more easily provide supplemental fixation without the need to reposition the patient, and without multiple tools extending from the surgical site.

Although examples of a spinous process implant and associated instruments and techniques have been described and illustrated in detail, it is to be understood that the same is intended by way of illustration and example only and is not to be taken by way of limitation. Accordingly, variations in and modifications to the spinous process implant, instruments, and technique will be apparent to those of ordinary skill in the art, and the following claims are intended to cover all such modifications and equivalents.

We claim:

1. An implant for placement between spinous processes of a spine comprising:
    a spacer comprising a first end, a second end with a second end terminal edge, and a sidewall therebetween with an elongated slot, wherein the elongated slot passes through the sidewall into an interior cavity defined within the sidewall of the spacer,
    a first extension having a superior lobe, an inferior lobe, a main body, and an aperture in the main body in cooperation with the interior cavity of the spacer, the first extension projecting outwardly from the first end of the spacer, wherein the spacer is fixed to a medial surface of the first extension at the first end of the spacer; and a second extension having a superior lobe, an inferior lobe, and a span connecting the superior and inferior lobes of the second extension, the second extension having a post extending into the elongated slot of the spacer to form a first mechanical lock to connect the second extension to the spacer, wherein the second extension is able to pivot about the spacer relative to a longitudinal axis extending through the spacer prior to the second extension being locked to the spacer, and wherein a medial surface of the second extension is slidable onto the second end with the second end terminal edge of the spacer, wherein the first extension is fixed to the spacer by means of a second mechanical lock, and wherein the spacer includes at least one protrusion extending radially outward from the spacer to cooperatively engage a lock groove portion of the second mechanical lock.

2. The implant of claim 1, wherein the elongated slot extends from the first end to the second end terminal edge, wherein the first and second extensions comprise the medial surface and a lateral surface opposite the medial surface, and wherein at least one of the first and second extensions contains fenestrations between the medial surface and the lateral surface to facilitate tissue in-growth.

3. The implant of claim 1, wherein the first and second extensions each comprise the medial surface and a lateral surface opposite the medial surface, and wherein at least one of the medial surfaces of the first and second extensions comprises a concavity to facilitate tissue in-growth.

4. The implant of claim 1, wherein the first mechanical lock engages a convex side of the sidewall.

5. The implant of claim 4, wherein the second extension comprises a lock bore and a lock fastener, the lock fastener comprising a head and a shaft wherein the head is rotationally received in the lock bore and the shaft forms the post that extends into the elongated slot, and wherein rotation of the lock fastener within the lock bore locks the second extension to the spacer.

6. The implant of claim 5, wherein the lock fastener further comprises a nut such that rotation of the lock fastener causes the nut to clamp the lock fastener to a sidewall of the spacer.

7. The implant of claim 1, wherein the at least one protrusion and lock groove portion taper to form a taper lock.

8. The implant of claim 1, further comprising a lock washer disposed between the first extension and the spacer to provide a friction fit upon rotation of the at least one protrusion into the lock groove portion.

9. The implant of claim 1, wherein the spacer comprises at least one detent and the second mechanical lock comprises a corresponding at least one tab extending radially inward to cooperatively engage the at least one detent.

10. The implant of claim 1, wherein the aperture fully encircles the spacer.

11. An implant for placement between spinous processes of a spine comprising:

a spacer formed by a sidewall with a convex exterior surface, the spacer comprising a first end and a second end distal from the first end, the sidewall comprising an anterior aspect, a superior aspect, a posterior aspect, and an inferior aspect, wherein an interior surface of the sidewall defines a cavity that is concave within the spacer, and wherein the cavity is accessible via an elongated slot that passes through the inferior aspect of the sidewall;

a first extension fixed to the spacer at the first end of the spacer, wherein the first extension includes at least one tab extending radially inward to cooperatively engage at least one detent along the first end of the spacer; and a second extension movably received within the elongated slot on the second end of the spacer at a terminal edge thereof, the second extension translatable over the sidewall and lockable to the spacer, wherein the first and second extensions each comprise a medial surface and a lateral surface opposite the medial surface, and wherein at least one of the first and second extensions contains fenestrations between the medial surface and the lateral surface to facilitate tissue in-growth.

12. The implant of claim 11, wherein the first end and the second end of the spacer form opposed openings perpendicular to a longitudinal axis extending through the spacer, the spacer comprising at least one additional opening in the sidewall in communication with an interior of the spacer to facilitate tissue in-growth.

13. The implant of claim 11, wherein at least one of the medial surfaces of the first and second extensions comprises a concavity to facilitate tissue in-growth.

14. The implant of claim 11, wherein the spacer includes fenestrations to facilitate tissue in-growth.

15. An implant for placement between spinous processes of a spine comprising:

a spacer comprising a first end, a second end with a second end terminal edge, and a sidewall with an elongated slot extending between the first end and the second end terminal edge, wherein the elongated slot passes through the sidewall into an interior cavity of the spacer;

a first extension comprising a superior lobe, an inferior lobe, a main body, and an aperture connected with the interior cavity of the spacer, the first extension fixed to the spacer at a plane transverse to a longitudinal axis of the spacer; and a second extension comprising a superior lobe, an inferior lobe, and a span connecting the superior and inferior lobes of the second extension, the second extension comprising a post extending into the elongated slot to form a mechanical lock to connect the second extension to the spacer.

16. The implant of claim 15, wherein the first extension is fixed to the spacer via a lock groove disposed on an inner sidewall of an aperture of the main body of the first extension that cooperatively engages at least one protrusion of the spacer, wherein the at least one protrusion extends outward along a sidewall of the first end, wherein the first and second extensions comprise a medial surface and a lateral surface opposite the medial surface, and wherein at least one of the first and second extensions contains fenestrations between the medial surface and the lateral surface to facilitate tissue in-growth.

17. The implant of claim 15, wherein the first and second extensions comprise a medial surface and a lateral surface opposite the medial surface, and at least one of the medial surfaces comprises a concavity to facilitate tissue in-growth.

18. The implant of claim 15, wherein the mechanical lock comprises a lock bore and a lock fastener, the lock fastener comprising a head and a shaft wherein the head is rotationally received in the lock bore and the shaft forms the post that extends into the elongated slot, and wherein rotation of the lock fastener within the lock bore locks the second extension to the spacer.

* * * * *